US008739602B2

(12) United States Patent
Vize et al.

(10) Patent No.: US 8,739,602 B2
(45) Date of Patent: Jun. 3, 2014

(54) PORTABLE ULTRAFINE PARTICLE SIZER (PUPS) APPARATUS

(75) Inventors: Andrew Vize, Wolcott, VT (US); Matthew Casari, Waterbury, VT (US); Britt Holmen, Burlington, VT (US); Jeff Frolik, Essex Junction, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 701 days.

(21) Appl. No.: 12/908,280

(22) Filed: Oct. 20, 2010

(65) Prior Publication Data

US 2012/0099105 A1 Apr. 26, 2012

(51) Int. Cl.
*G01N 15/02* (2006.01)

(52) U.S. Cl.
USPC ........................................ 73/28.02; 73/28.04

(58) Field of Classification Search
USPC .................................. 73/28.01, 28.02, 28.04
See application file for complete search history.

(56) References Cited

U.S. PATENT DOCUMENTS

| | | | | |
|---|---|---|---|---|
| 6,544,484 | B1 * | 4/2003 | Kaufman et al. | 422/186.04 |
| 6,639,671 | B1 * | 10/2003 | Liu | 356/336 |
| 7,880,109 | B2 * | 2/2011 | Okuda et al. | 209/129 |
| 2002/0047713 | A1 * | 4/2002 | Noll | 324/464 |
| 2006/0093737 | A1 * | 5/2006 | Dick et al. | 427/180 |
| 2009/0173670 | A1 * | 7/2009 | Okuda et al. | 209/127.1 |
| 2010/0001184 | A1 * | 1/2010 | Chen et al. | 250/307 |

* cited by examiner

*Primary Examiner* — Daniel S Larkin

(57) ABSTRACT

The Portable Ultrafine Particle Sizer (PUPS) invention is provided. The PUPS is an instrument which can measure particle number concentration for particle sizes under 200 nanometers in-situ. The PUPS is a compact design for quick mounting on vehicles. Size discrimination is accomplished using a compact reverse Differential Mobility Analyzer (rDMA). Particle charging is accomplished using corona ionization. Concentration measurements are completed using a unique flexible printed circuit board electrode which can be removed for cleaning, disposal or chemical analysis of collected particles at the end of its in situ measurement life.

8 Claims, 15 Drawing Sheets

PORTABLE ULTRAFINE PARTICLE SIZER (PUPS) APPARATUS

REFERENCE TO U.S. GOVERNMENT INTEREST

"The U.S. Government has a paid-up license in this invention and the right in limited circumstances to require the patent owner to license others on reasonable terms as provided for by the terms of Grant DTRT06-G-0018 awarded by U.S. Department of Transportation."

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related. Application(s) to the extent such subject matter is not inconsistent herewith.

U.S. provisional patent application 61/279,460, entitled "Portable Ultrafine Particle Sizer", naming Andrew Vize, Matthew Casari, Britt Holmen, and Jeff Frolik, as inventors, filed 21 Oct. 2009.

BACKGROUND

1. Field of Use

This application relates to the measurement of air pollution and in particular to the rapid measurement of the quantity and size distribution of aerosol particles. As vehicle engines become more complex and varied, it becomes necessary to have better systems to determine our motor vehicle emissions inventories. To develop accurate ultrafine particle models, the common practice of using engine dynamometers and in-lab testing will need to be replaced with in-situ monitoring of vehicles on the road. However, measurement of engine exhaust particle size is currently done using instruments that are too bulky, expensive, and power inefficient to easily adapt to on-board, in-situ particle measurement.

2. Description of Prior Art (Background)

There are several limitations with current systems for measuring engine exhaust particles, in particular ultrafine particles, or particle diameters less than 100 nanometers. Measuring ultrafine particulate is typically done in a laboratory setting. Particulate monitoring instruments are bulky and not designed for in-situ (i.e., on board and real-time) particulate monitoring. Those particulate sizing instruments are generally connected to engine dynamometers which are operated at loads to roughly simulate on-road conditions and are not suitable for in-situ fleet-wide monitoring of engine exhaust particles.

In one optical system, light is directed through aerosol particle-laden smoke and the attenuation of the light is measured on a detector to indicate total particle concentration. This method does not measure particle size distribution, however. Another optical method uses light scattering to measure particle size by causing the particles to pass one at a time through a chamber so that scattered light amplitude depends on the particle size. The amplitude is measured by a photomultiplier which produces an electrical signal dependent upon particle size. To isolate single particles for detection, gas sampling must be done at low velocity, and the system is usually provided with very narrow pipes which are subject to contamination, require frequent cleaning, and tend to collect the larger particles before their entry into the sensing chamber. Further, such method of measuring the size of a single particle is quite slow, requiring perhaps as much as an hour for a typical measurement.

Electrical methods have the advantage that they can be operated nearly continuously with the results available to the operator after a very short interval of time. In one electrical Method described in U.S. Pat. No. 3,114,877 to Dunham, a charging device operates to charge separate groups of aerosol particles passing the device. The particles then flow in a random manner through a field-free region, pass an ion trap and flow to a detector. At the detector, the particles lose their charge and produce a current. Although the detector current in the Dunham apparatus is said to be an index of the number of particles, it is clear that the amplitude of the current is a function of the total charge on all of the particles sensed by the detector at a given moment. Thus, the amplitude of the current is a function of the total surface area of the particles. Because the particles flow in a random, manner to the detector, particles having different surface areas (and thus different sizes) lose their charge at the same moment of time to produce the current. Therefore, the output current in the Dunham apparatus is not indicative of the number of particles except when they are of uniform size.

Another method which indicates aerosol particle size distribution is based on the mobility of charged particles in an electric field extending radially across a tube in which the particles flow. Mobility is a measure of the velocity of a charged particle in an electric field, and generally speaking, the higher the charge on the particle the higher the mobility. For a given method of charging a particle, the amount of charge on the particle is a function of the size of the particle. Therefore, mobility is a function of particle size and methods based on particle mobility utilize the difference in mobility to measure particle size distribution. In one such device described in U.S. Pat. No. 3,413,545 to Whitby, clean air is caused to move downwardly in an annular flow path surrounding an elongated electrode extending axially in a cylindrical housing. Charged aerosol particles are introduced around the outer periphery of the flow path of clean air and an electric potential is applied across the elongated electrode and the cylindrical housing. For any given potential, particles having mobility below a certain value will not move far enough radially to contact and lose their charge to the elongated electrode before passing its downstream end. An electrometer detects these charged particles which generate a current, the amplitude of which is a function of the total charge on the detected particles. By varying the potential applied to the elongated electrode, more or fewer charged particles will reach the detector and induce the current. By relating the current produced when various potentials are applied to the elongated electrode, a measure of particle size distribution can be obtained. However, a number of factors limit the usefulness of this device for monitoring effluents in stacks of industrial installations, for example. Due to the method of charging, known as diffusion charging, only particles less than about 2 microns diameter can be measured whereas in a typical stack, particles up to 100 microns or more will be present. Further, the diffusion charging method is also inconvenient because it requires a source of compressed air and various thin pipes which are subject to clogging.

Accordingly, there is a need for a method and apparatus for a compact, low-cost, low power system capable of discriminating and measuring in-situ particle size distribution based on particle mobility in an electric field utilizing a small volume differential mobility analyzer and disposable electrodes.

BRIEF SUMMARY

The foregoing and other problems are overcome, and other advantages are realized, in accordance with the presently preferred embodiments of these teachings.

In accordance with one embodiment of the present invention an apparatus for measuring aerosol particle concentration and particle size distribution is provided. The apparatus includes a corona ionizer utilizing a high voltage tungsten needle and a concentric ground ring for applying a negative high voltage potential to the aerosol particles. Also included is a reverse differential mobility analyzer (rDMA) for separating charged particles based on electrical mobility, wherein the rDMA includes a charged central repulsion electrode for driving the charged particles towards flexible printed circuit board detectors sized according to predetermined dimensions corresponding with particle sizes of interest.

In accordance with another embodiment of the present invention a portable ultrafine particle measuring apparatus for measuring aerosol particle concentration and particle size distribution is provided. The apparatus includes a corona ionizer for applying a negative charge via a negative high voltage potential to the aerosol particles. Also included is at least one conductive needle support having precision-machined flow pathways for the aerosol gas sample. The apparatus also includes a non-conductive needle support for supporting the tungsten needle and electrically insulating the conductive needle support from the ground ring electrode. The apparatus further includes a reverse differential mobility analyzer (rDMA) for separating charged particles based on electrical mobility. The rDMA contains a central repulsion electrode and flexible printed circuit boards (PCB) for detecting charged particles. Included in the apparatus is a converter for converting the detected current induced by charged particles to a digital signal.

The invention is also directed towards a portable ultrafine particle sizer system for measuring sizes of particles in an aerosol gas sample. The system includes a pump and a proportional valve for pumping aerosol gas samples through the system. A flow meter connectable to at least one pump measures aerosol gas flow through rates set by the pump and the proportional valve. A positive or negative corona ionizer with a tungsten needle ionizes particles within the aerosol gas sample and the reverse differential mobility analyzer (rDMA) determines particle size distribution based upon the ionized particles and separates the particles based upon different electrical mobility.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

Figure 1:
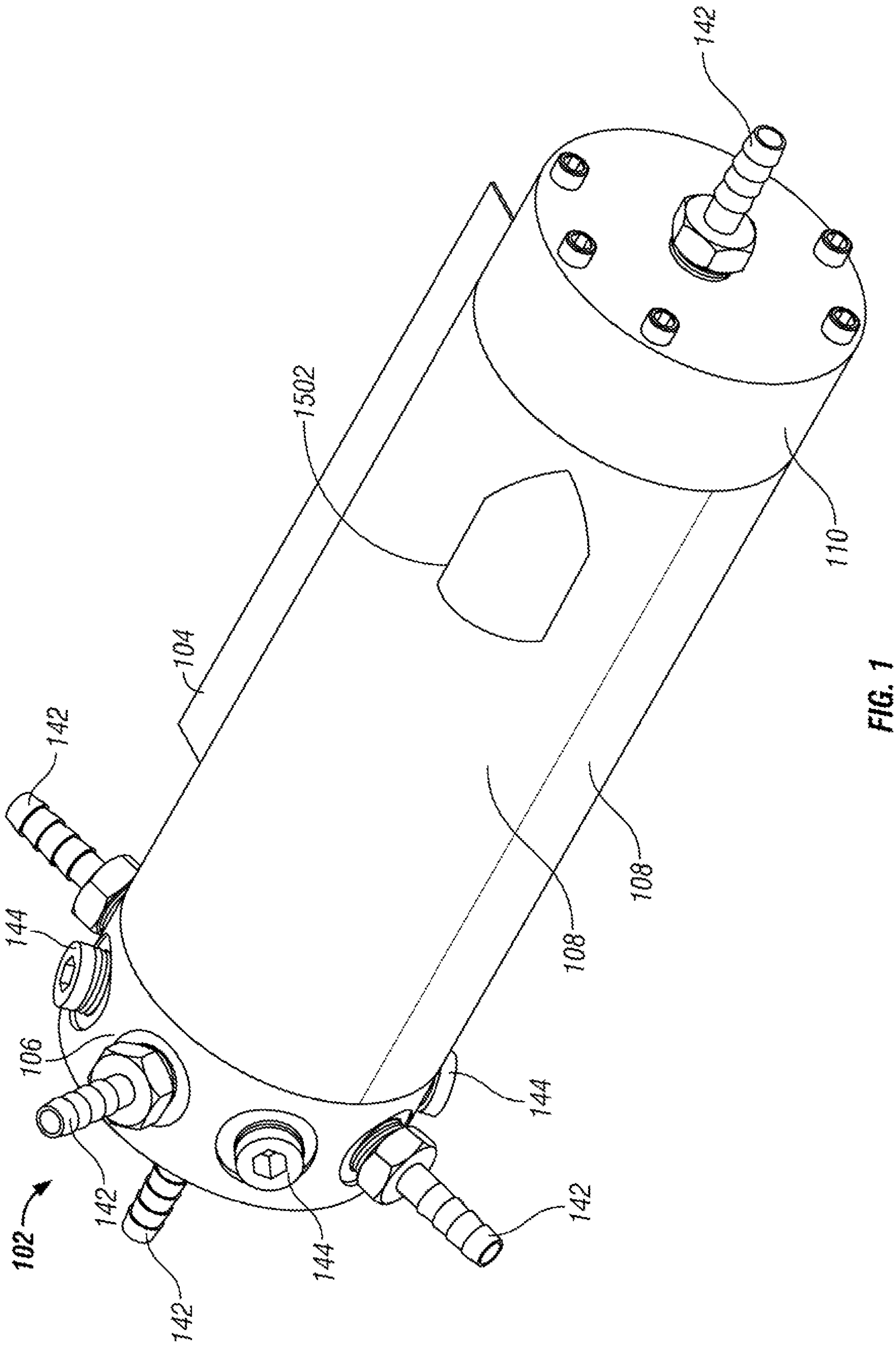
FIG. 1 is a pictorial illustration of one embodiment of the Portable Ultrafine Particle Sizer (PUPS) apparatus in accordance with the present invention.

Referring now to FIG. 1 there is shown a pictorial illustration of one embodiment of the Portable Ultrafine Particle Sizer (PUPS) Assembly 102. The PUPS assembly includes Flexible Printed Circuit Board (flex-PCB) 104, Sheath Gas Injection Module 106, rDMA housing 108, aluminum end cap 110, fasteners 144, and push-on hose fittings 142. It will be understood throughout that fittings 142 may be any suitable push-on hose fitting or any other suitable hose connector. Likewise plugs 144 may be any suitable mechanical plug. The sheath gas injection module 106 provides concentric alignment of the corona ionizer (See FIG. 7-702 ), sheath gas flow straightener (See FIG. 2-212), repulsion electrode (See FIG. 2-214), and rDMA housing 108. The sheath gas injection module 106 also serves the dual purpose of creating a constant gas pressure across the surface of the sheath gas flow straightener (See FIG. 2-212). The rDMA housing 108 is generally comprised of polypropylene material; however, it will be understood that the rDMA housing 108 could be any structurally and chemically stable non-conductive material. The rDMA housing 108 is designed to provide precise alignment of the flex-PCB (See FIG. 14-1402) along the length and radius of the rDMA housing 108, and provide the sealed pneumatic environment.

The PUPS 102 is a composite of aluminum, PTFE TEFLON, polypropylene and tungsten. However, it will be understood that any suitable metal or material having characteristics similar to, or exceeding, one or more material characteristics associated with aluminum, PTFE TEFLON, polypropylene, or tungsten may be used. The PUPS assembly is comprised of two main parts, a corona ionizer (See FIG. 7-702) and a reverse differential mobility analyzer (rDMA) 108. In the corona ionizer (See FIG. 7-702) a negative high voltage potential is applied from a tungsten needle (See FIG. 8-824) to a concentric ground ring electrode (See FIG. 8-822). Electrons are generated in the localized atmospheric breakdown around the tungsten needle (See FIG. 8-824). These electrons drift outward and become attached to the aerosol particles passing through the corona ionizer (See FIG. 7-702), thus creating negatively charged aerosol particles.

In the rDMA 108 a negative high voltage potential is applied from a central repulsion electrode (See FIG. 2-214) to a concentric ground cylinder. Particles entering the rDMA 108 are repelled away from this central rod 214 by electrostatic force toward a series of ring electrodes. The PUPS 102 is designed to separate particles based on aerosol diameters between approximately 10 nm and 200 nm. Smaller particles are repelled more readily than particles that are larger comparatively and impact the ring electrode upstream, respectively (See FIG. 13-1340).

Figure 2:
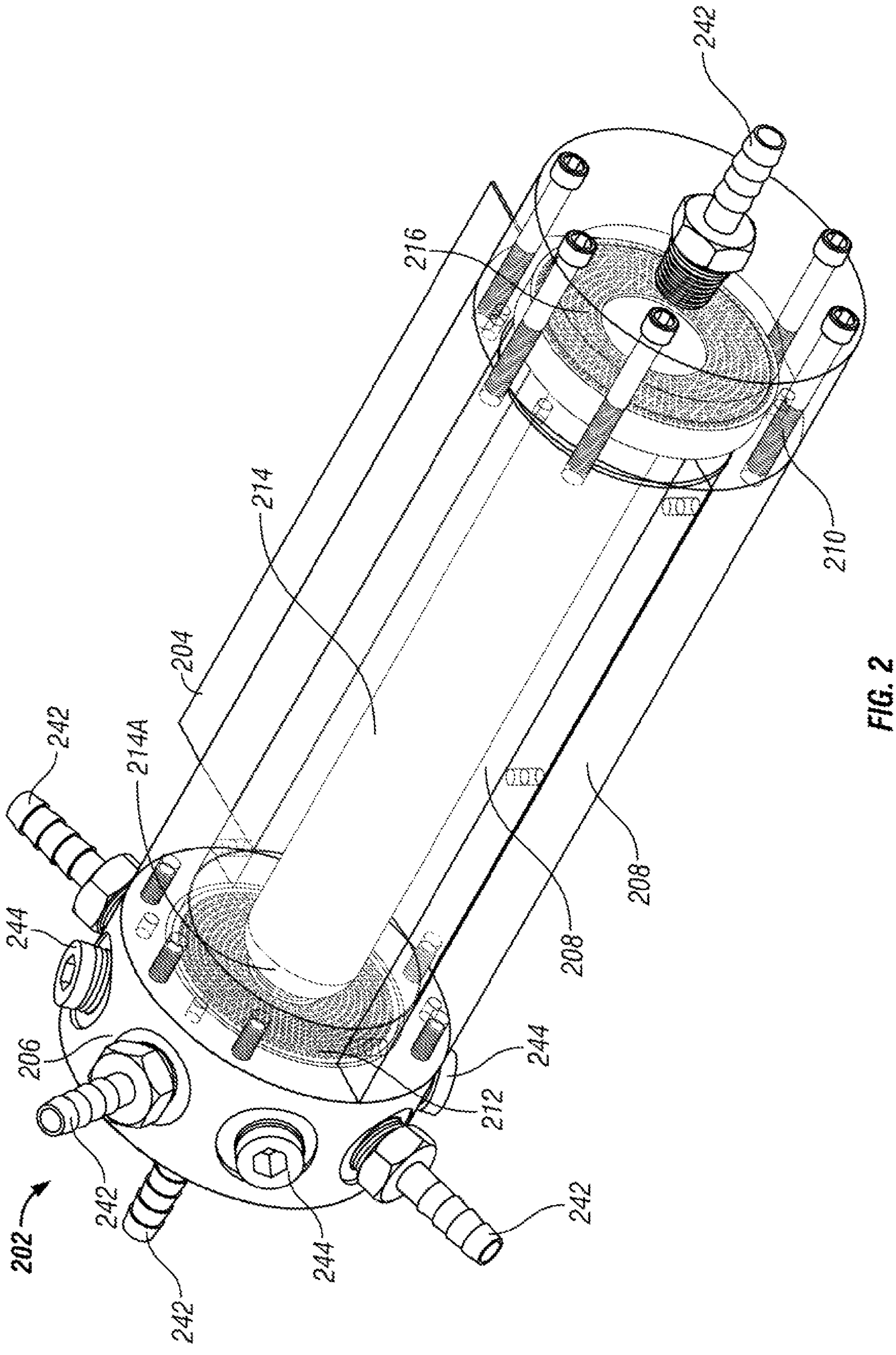
FIG. 2 is a transparent illustration of the PUPS invention shown in FIG. 1.

The end cap 110 provides alignment of the repulsion electrode (214) and the exhaust gas flow straightener (See FIG. 2-216). The conical internal surface of the end cap 110 promotes constant gas pressure across the face of the exhaust gas flow straightener (See FIG. 2-216).

Referring also to FIG. 2 there is shown a transparent illustration 202 of the PUPS invention shown in FIG. 1. Included in this illustration is—Flexible Printed Circuit Board (flex-PCB) 204—See Item 1402, Sheath Gas Injection Module 206 (See also FIG. 1-106, rDMA housing 208 (See also FIG. 1-108), End Cap 210 (See also FIG. 1-110), and Electrical Grade PTFE TEFLON Sheath Gas Flow straightener 212. The sheath gas flow straightener 212, with an array of holes, induces fluid flows in parallel layers. The sheath gas flow straightener 212 is designed to promote laminar flow of sheath gas as it enters the rDMA 208. It will be further understood throughout that fittings 242 may be any suitable push-on hose fitting or any other suitable hose connector. Likewise plugs 244 may be any suitable mechanical plug.

Still referring to FIG. 2, there is shown aluminum repulsion electrode 214. The repulsion electrode 214 is a cylindrical rod of suitably conductive material with known dimensions. A negative high voltage is applied to the electrode 214 thus inducing a repulsive electrostatic force on the negatively charged aerosol particles. Also shown is Electrical Grade PTFE TEFLON Exhaust Gas Flow Straightener 216. The exhaust gas flow straightener is a round disk with an array of holes through it. It is designed to promote constant flow of gas through radial cross section of the rDMA 208. Still referring to FIG. 2, there is shown the Glass Filled Polyetheretherketone Aerosol Injection Manifold 214A. The aerosol injection manifold 214A serves the dual purpose of centering the repulsion electrode 214 in the exit of the corona ionizer (See FIG. 7-702) and it promotes tracking of the aerosol streamlines along the surface of the repulsion electrode 214 while no electrostatic forces are applied.

Figure 3:
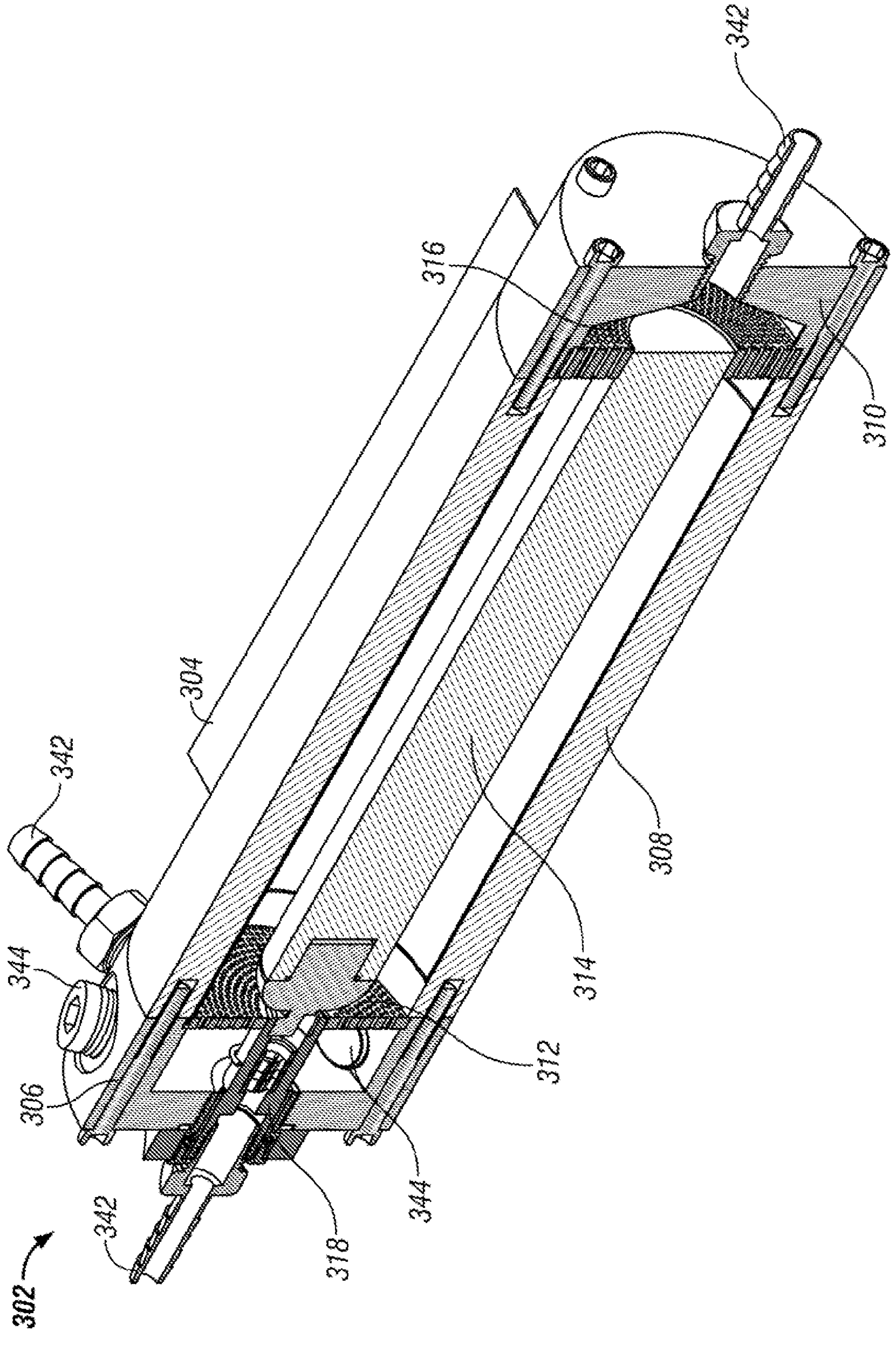
FIG. 3 is a transparent cross sectional illustration of the invention shown in FIG. 1.

Referring also to FIG. 3, there is shown a cross sectional view of the complete PUPS Assembly 302. FIG. 3 illustrates the spatial relationship of flexible printed circuit board 304, sheath gas injection module 306 (See FIG. 1-106), rDMA housing 308 (See FIG. 1-108), End Cap 310 (See FIG. 1-110), Sheath Gas Flow Straightener 312 (See FIG. 2-212), Repulsion Electrode 314 (See FIG. 2-214), Exhaust Gas Flow Straightener 316 (See FIG. 2-216), and Corona Ionizer Housing 318 (See FIG. 7-726). It will be understood throughout that fittings 342 may be any suitable push-on hose fitting or any other suitable hose connector. Likewise plugs 344 may be any suitable mechanical plug.

Figure 4:
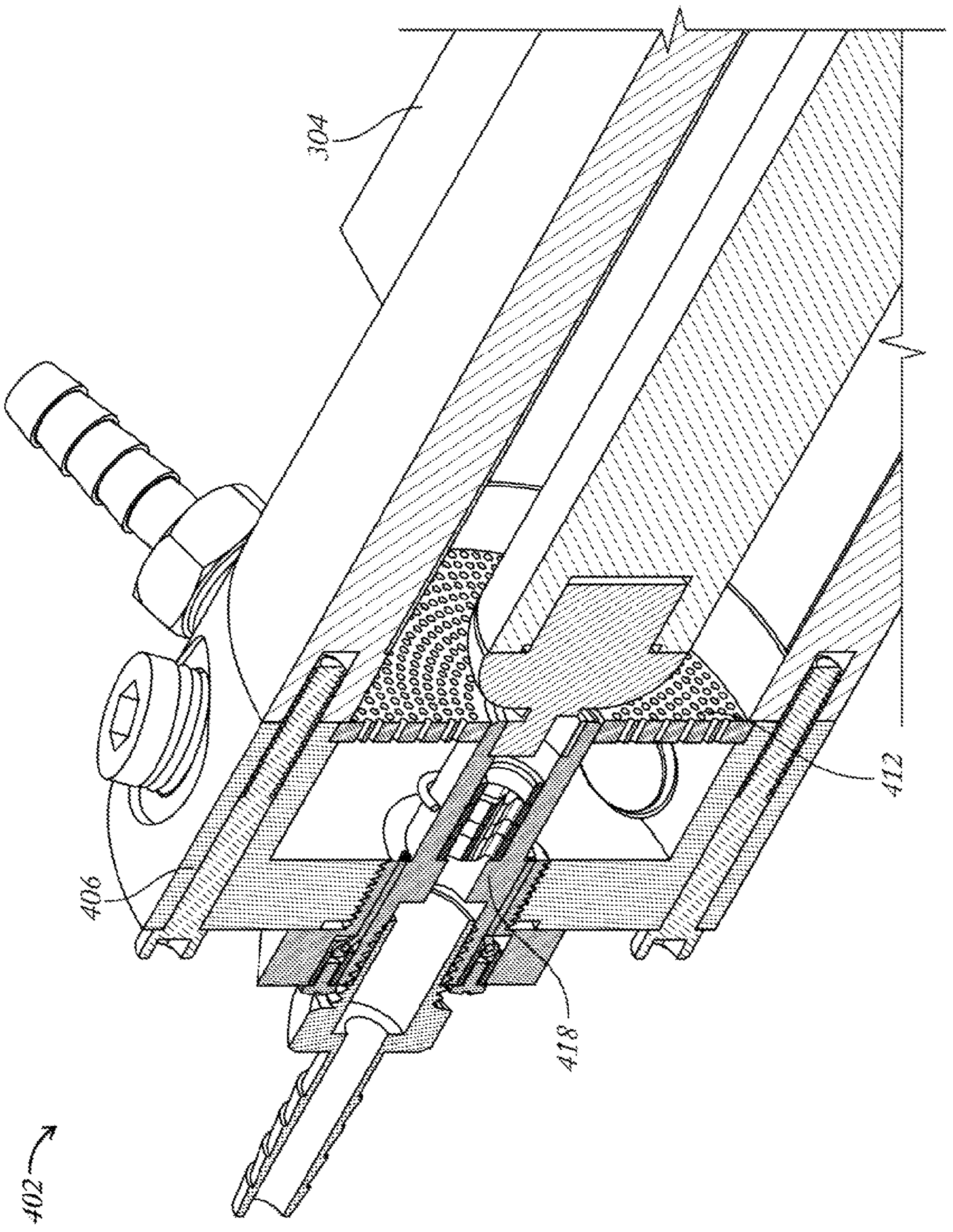
FIG. 4 is an enlarged transparent cross sectional illustration of the input port end of the invention shown in FIG. 3.

Referring also to FIG. 4, there is shown a zoomed partial cross section 402 of the PUPS Assembly 102. FIG. 4 illustrates the spatial relationship of Sheath Gas Injection Module 406 (See FIG. 1-106), Sheath Gas Flow Straightener 412 (See FIG. 2-212), and Corona Ionizer Housing 418 (See FIG. 7-726). It will be understood throughout that fittings 442 may be any suitable push-on hose fitting or any other suitable hose connector. Likewise plugs 444 may be any suitable mechanical plug.

Figure 5:
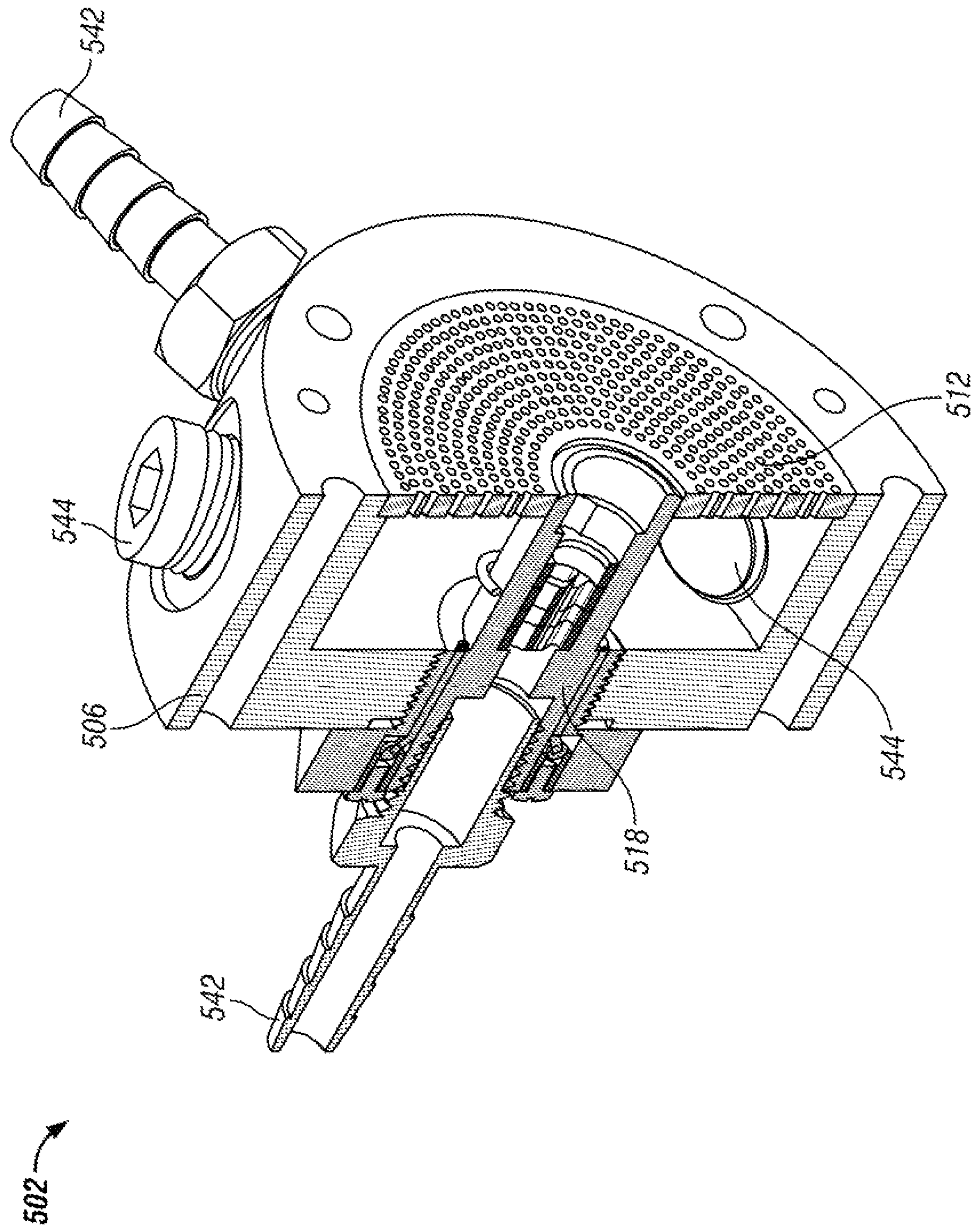
FIG. 5 is a cross sectional illustration of the Corona Ionizer & Sheath Air Injection Module in accordance with the invention shown in FIG. 4.

Referring also to FIG. 5, there is shown a Cross Sectional View 502 of Corona Ionizer (See FIG. 7-702) and Sheath Air Injection Module 506 (See FIG. 1-106). FIG. 5 further illustrates the spatial relationship of the Sheath Gas Injection Module 506 (See FIG. 1-106), the Sheath Gas Flow Straightener 512 (See FIG. 2-212), and the Corona Ionizer Housing 518 (See FIG. 7-726). It will be understood throughout that fittings 542 may be any suitable push-on hose fitting or any other suitable hose connector. Likewise plugs 544 may be any suitable mechanical plug.

Figure 6:
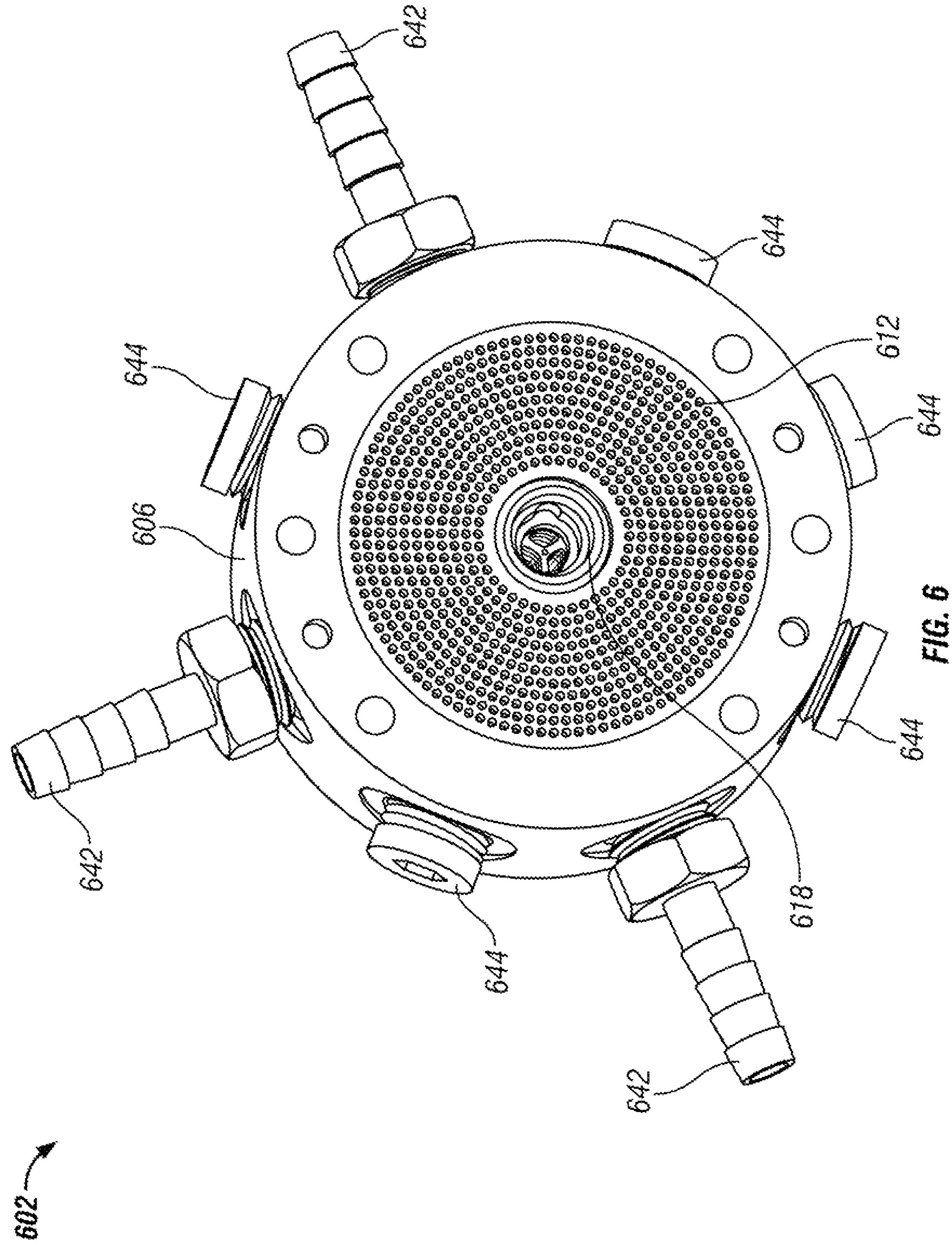
FIG. 6 is a rotated illustration of the Corona ionizer & Sheath Air Injection Module shown in FIG. 5.

Referring also to FIG. 6, there is shown a Rotated View 602 of Corona Ionizer 502 (See FIG. 7-702) and Sheath Air Injection Module 606 (See FIG. 1-106). FIG. 6 further illustrates the spatial relationship of the Sheath Gas Injection Module 606 (See also FIG. 1-106), Sheath Gas Flow Straightener 612 (See also FIG. 2-212), and Corona Ionizer Housing 618 (See also FIG. 7-726). It will be understood throughout that fittings 642 may be any suitable push-on hose fitting or any other suitable hose connector. Likewise plugs 644 may be any suitable mechanical plug.

Figure 7:
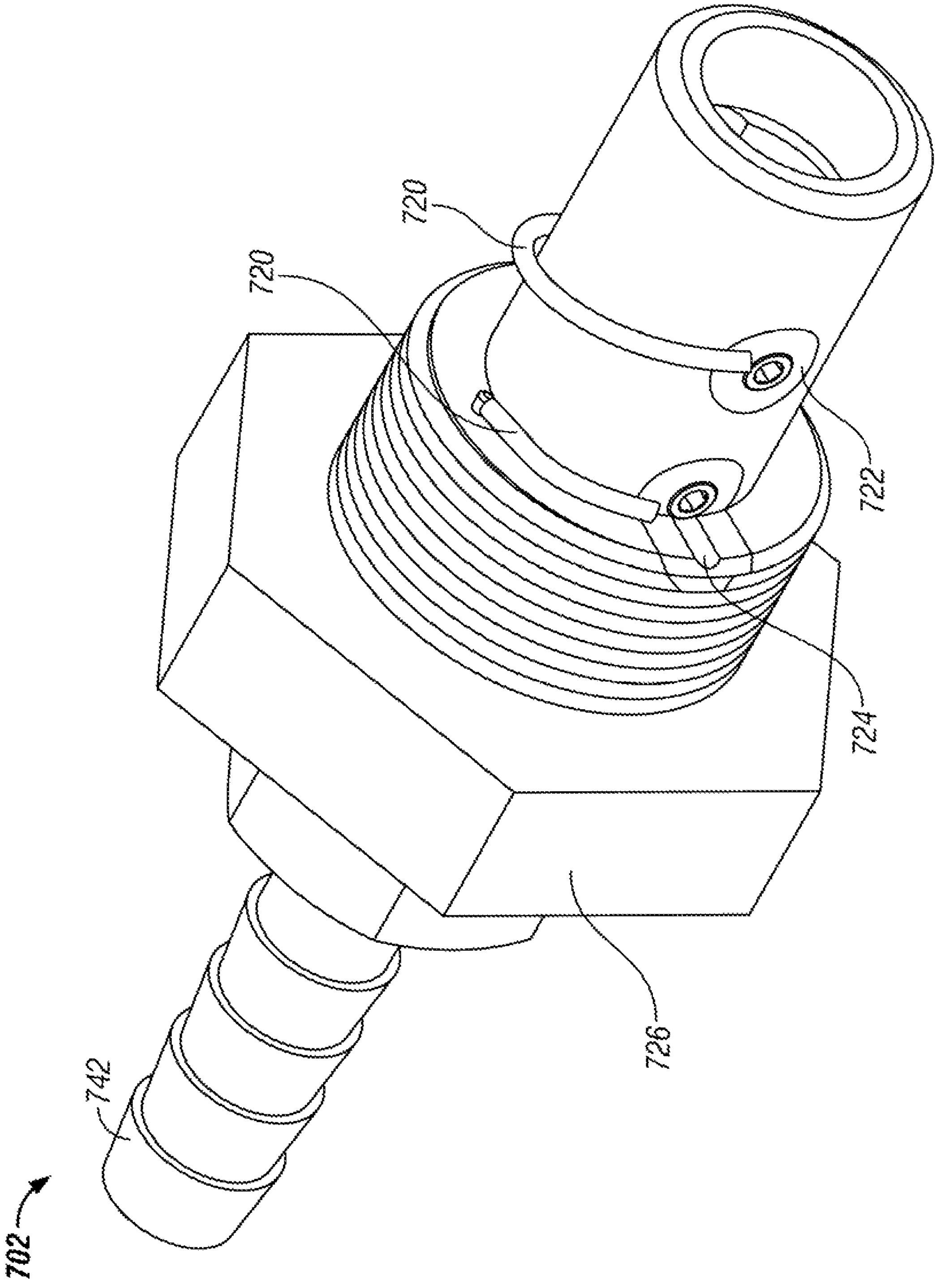
FIG. 7 is a pictorial illustration of the Corona Ionizer module in accordance with the invention shown in FIG. 1.

Referring also to FIG. 7 there is shown a pictorial illustration of the Corona Ionizer module 702. The Corona Ionizer 702 is a composite of PTFE TEFLON, brass, copper buss wire, aluminum, and tungsten. Aerosol passing through the corona ionizer 702 passes through a cloud of free electrons induced by a localized breakdown in the atmosphere surrounding a tungsten corona needle (See FIG. 8-824). A flow of negatively charged aerosol particles exit the corona ionizer 702.

Also shown in FIG. 7 are Plated Copper Electrical Buss Wires 720. These wires make electrical contact between the electrodes of the corona ionizer 702 and the external screw connectors. FIG. 7 also shows Stainless Steel Ground Set Screw and Brass Fitting 722, this brass insert and set screw 722 hold the ground ring electrode (See FIG. 8-822) in place and creates the electrical connection; High Voltage Set Screw and Brass Fitting 724, this brass insert and set screw hold the conductive corona needle support (See FIG. 8-828) in place and creates the electrical connection; and PTFE TEFLON Corona Ionizer Housing 726, this housing provides a chemically resistant, sealed environment which provides electrical isolation for the negative high voltage potentials present.

Figure 8:
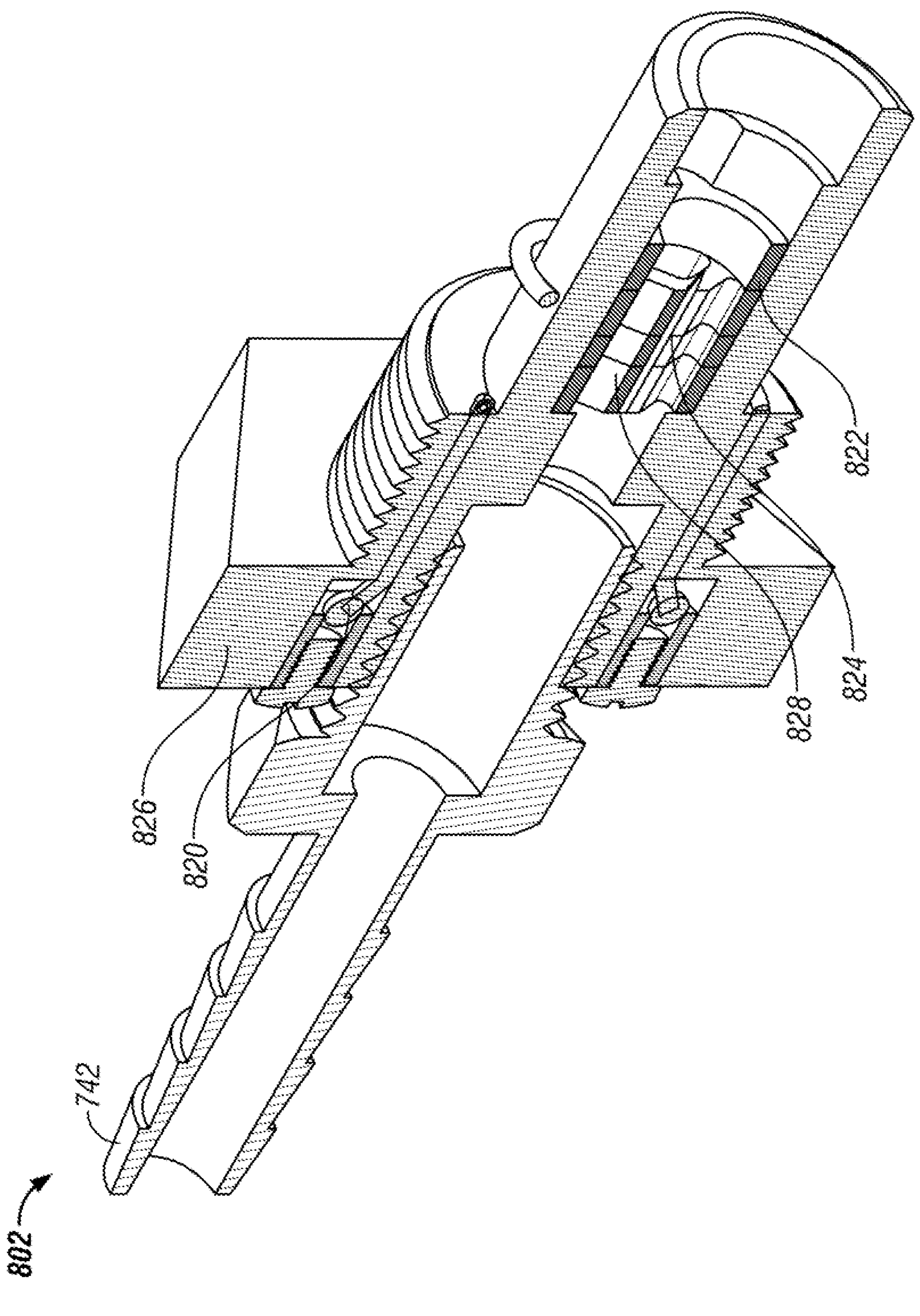
FIG. 8 is a cross sectional pictorial illustration of the Corona Ionizer module in accordance with the invention shown in FIG. 7.

Referring also to FIG. 8 there is shown a cross sectional view of the Corona Ionizer 802 (See also FIG. 7-702). Included in this view is Electrical Buss Wire 820 (See also FIG. 7-720) and TUNGSTEN corona needle 824. Also shown in FIG. 8 is Aluminum Ground Ring Electrode 822. This ring electrode is concentrically placed around the corona needle 824 and serves as a ground reference for the corona needle 824. The tip geometry of the needle 824 in reference to the ground ring electrode 822 creates an inhomogeneous electric field due to the negative high voltage potential difference applied. This produces a breakdown of the atmosphere localized around the tip of the needle 824. The PUPS unit 102 uses commercially available 7B TUNGSTEN probes from Micromanipulator to reduce fabrication cost. FIG. 8. also illustrates the spatial relationship of Corona Ionizer Housing 826 (See also FIG. 7-726) and Aluminum Corona Needle Support 828. This tri-spoke support 828 holds the corona needle in place and creates and electrical connection to the high voltage set screw and brass fitting (See also FIG. 7-724).

Figure 9:
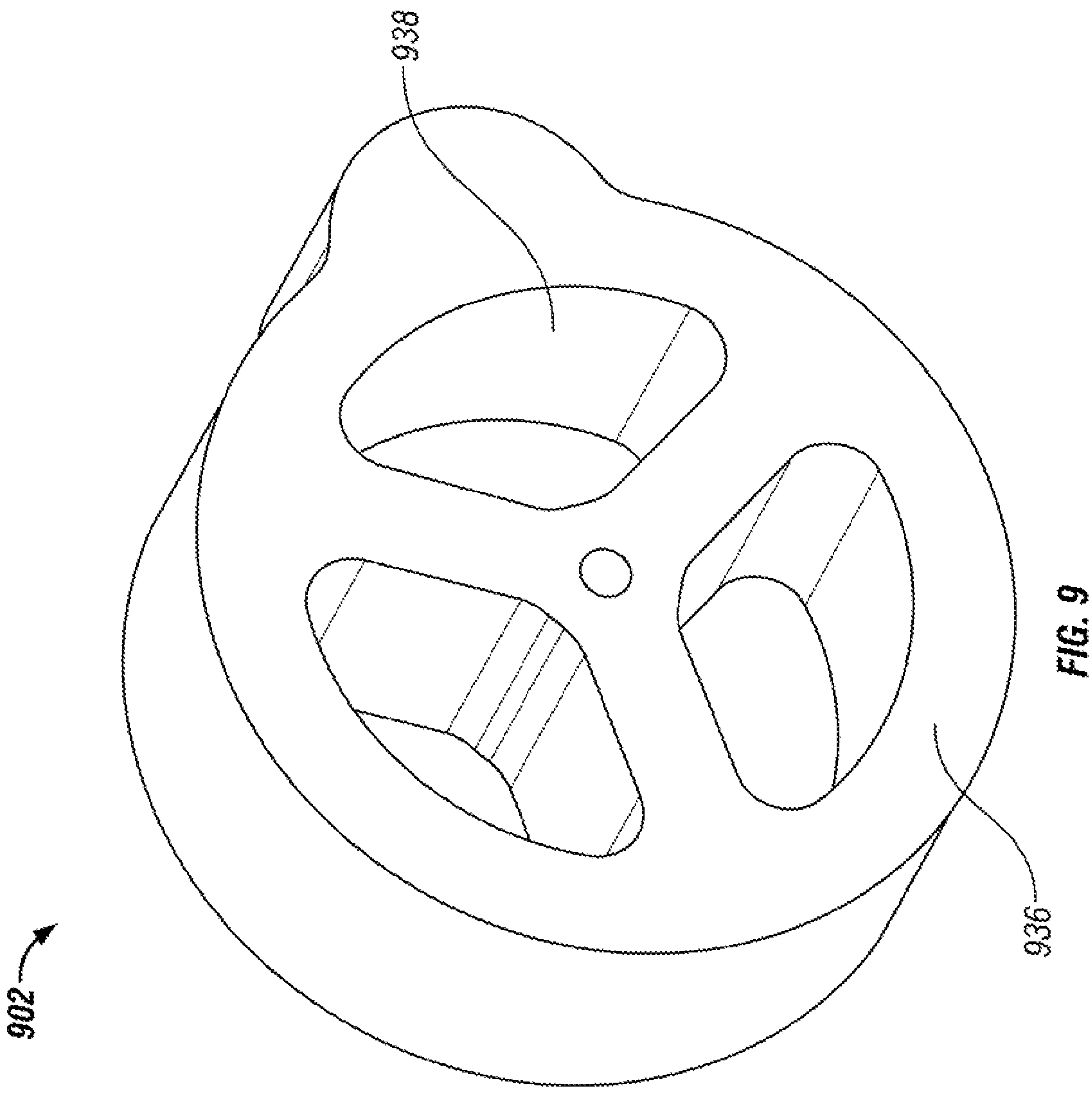
FIG. 9 is a pictorial illustration of the Corona needle support in accordance with the invention shown in FIG. 6.

Referring also to FIG. 9, there is shown a pictorial illustration of the Corona Needle Support 902 (Conductive & Non-Conductive; See FIG. 8-828 & FIG. 10-1032, respectively). Machined channels 938 provide the pathways through the structure of the corona needle support 936 for the aerosol to flow into the charging region of the corona ionizer (See FIG. 7-702). These channels 938 align with the channels of the mating corona needle support 902 due to an alignment key on the side of the unit 902.

Figure 10:
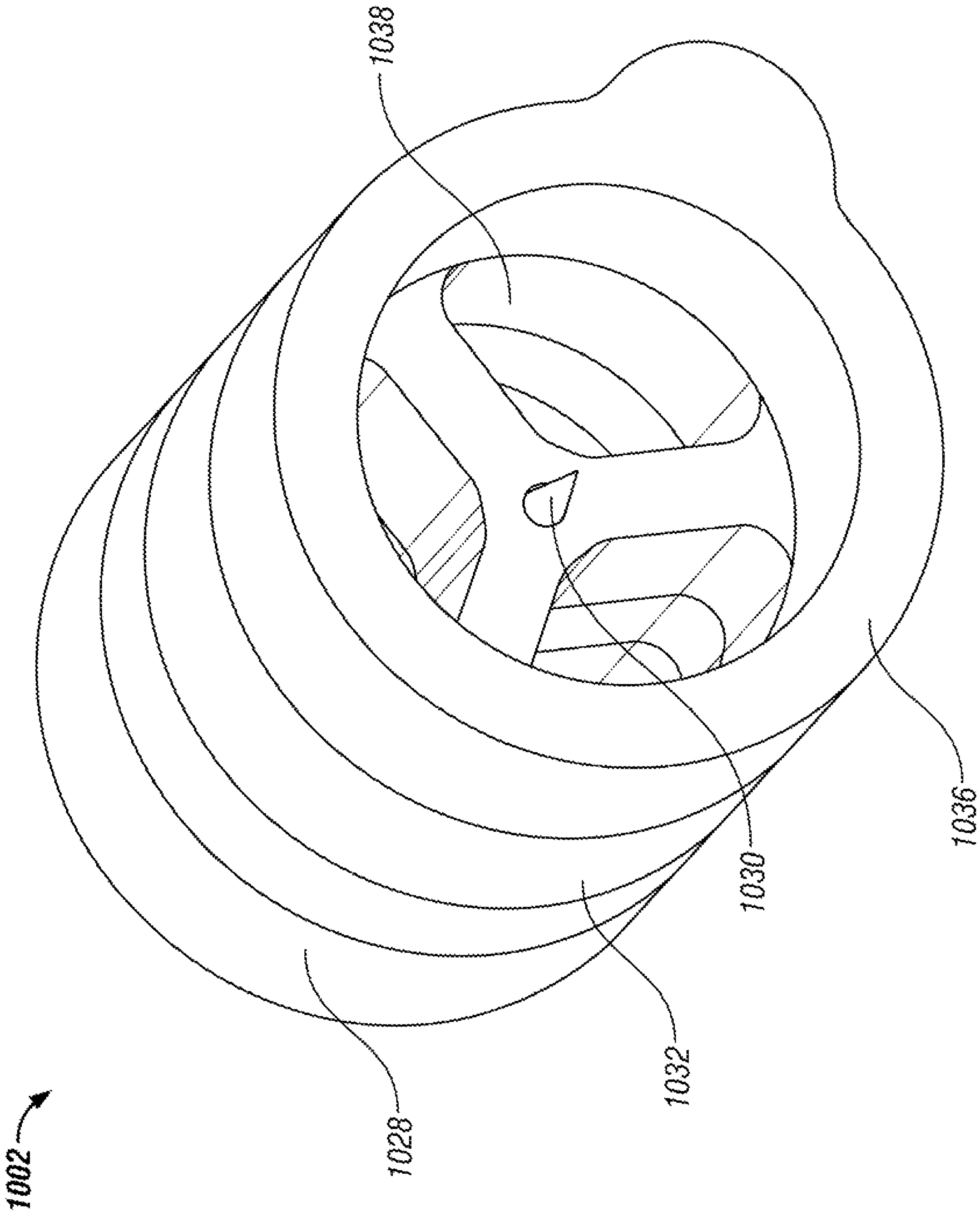
FIG. 10 is a pictorial illustration of the Corona Ionizer Internal Assembly in accordance with the invention shown in FIG. 1.

Referring also to FIG. 10, there is shown a pictorial illustration of the PTFE Teflon, Aluminum, and Tungsten Corona Ionizer Internal Assembly 1002. FIG. 10 further illustrates the spatial relationship of the Conductive Corona Needle Support 1028 (See also FIG. 8-828), the Corona Needle 1030 (See also FIG. 8-824), and the Electrical Grade PTFE Teflon Non-Conductive Corona Needle Support 1032. The Non-Conductive Corona Needle Support 1032 holds the corona needle (FIG. 8-824) in place and directs the aerosol flow around the localized atmospheric breakdown region occurring at the tip of the corona needle 1030. The support 1032 serves as an insulator between the conductive corona needle support (FIG. 8-828) and the ground ring electrode (FIG. 8-822). Also, shown is Ground Ring Electrode 1036 (See also FIG. 8-822 and Machined Channel 1038 (See also FIG. 9-938).

Figure 11:
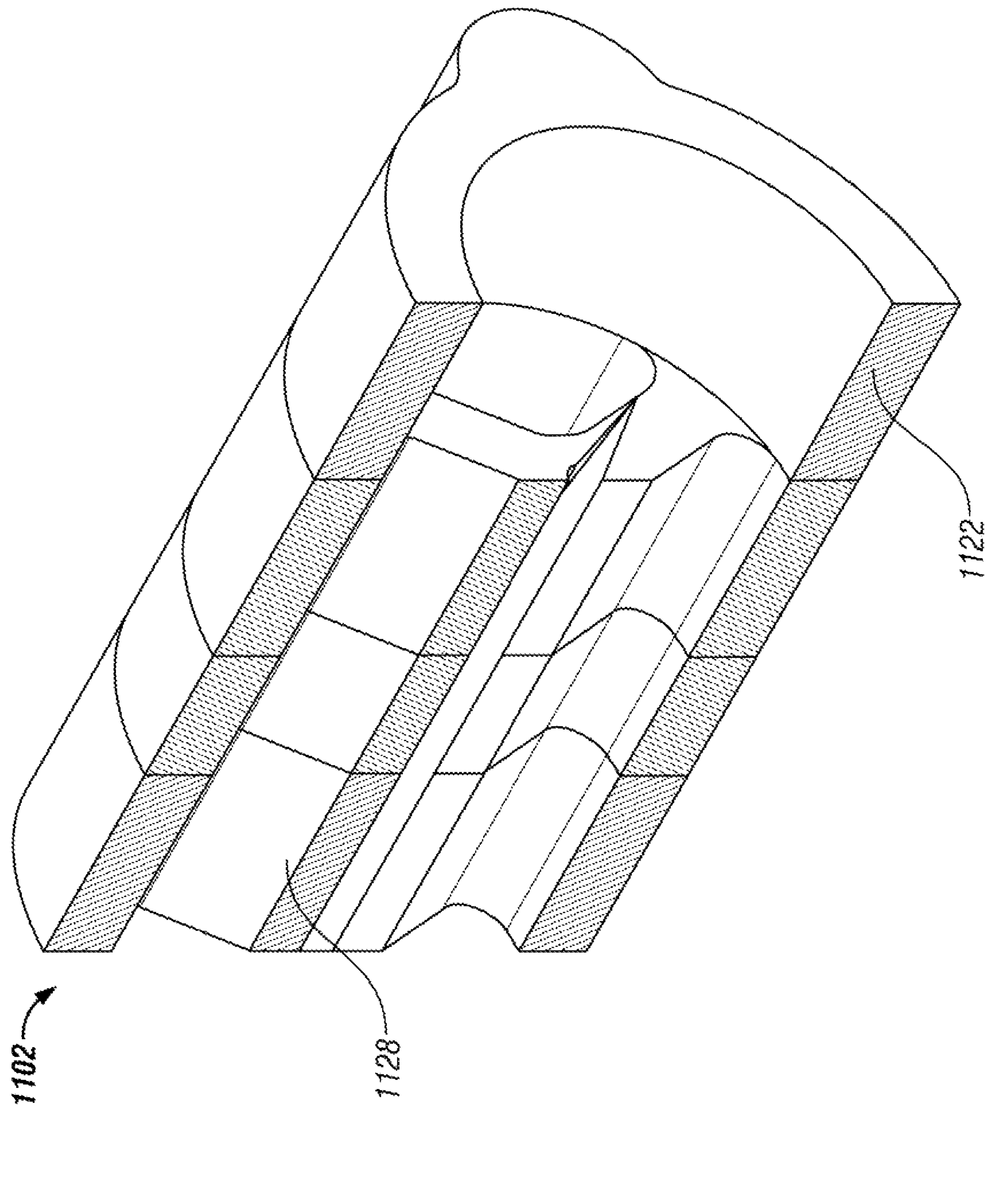
FIG. 11 is a pictorial illustration of a cross section of the Corona Ionizer Internal Assembly in accordance with the invention shown in FIG. 10.

Referring also to FIG. 11, there is shown a pictorial illustration of a cross section of the Corona Ionizer Internal Assembly 1102. Also shown in FIG. 11 are Conductive Corona Needle Support 1128 (See also FIG. 8-828) and Ground Ring Electrode 1122 (See also FIG. 8-822).

Figure 12:
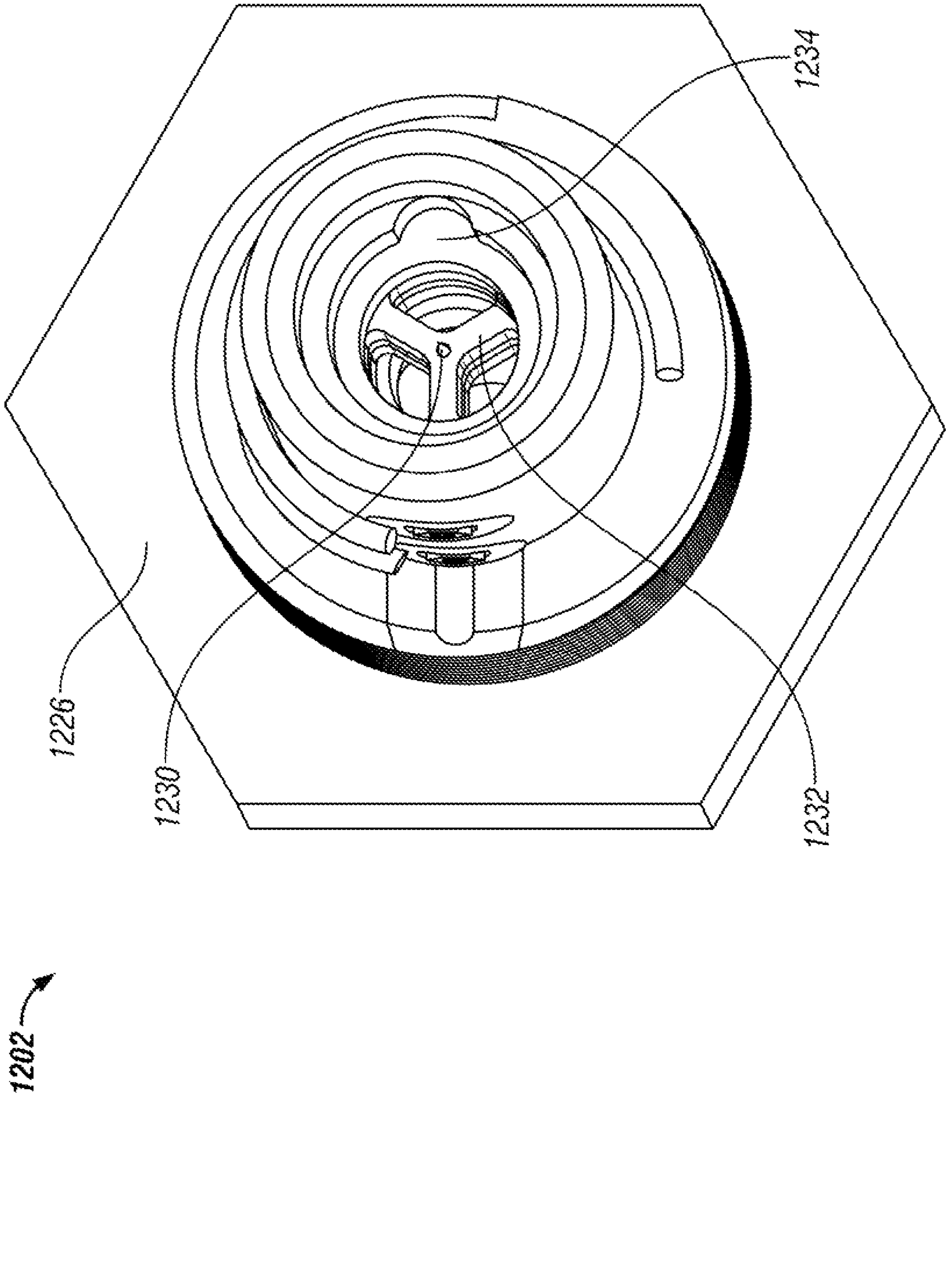
FIG. 12 is a rotated illustrated view of the Corona Ionizer shown in FIG. 7.

Referring also to FIG. 12, there is shown a rotated illustrated view of the Corona Ionizer 1202 (See also FIG. 7-702). Corona Ionizer Housing 1226 (See also FIG. 7-726); Corona Needle 1230 See also FIG. 8-824; Non-Conductive Corona Needle Support 1232 (See also FIG. 10-1032); and Ground Ring Electrode 1234 (See also FIG. 8-822).

Figure 13:
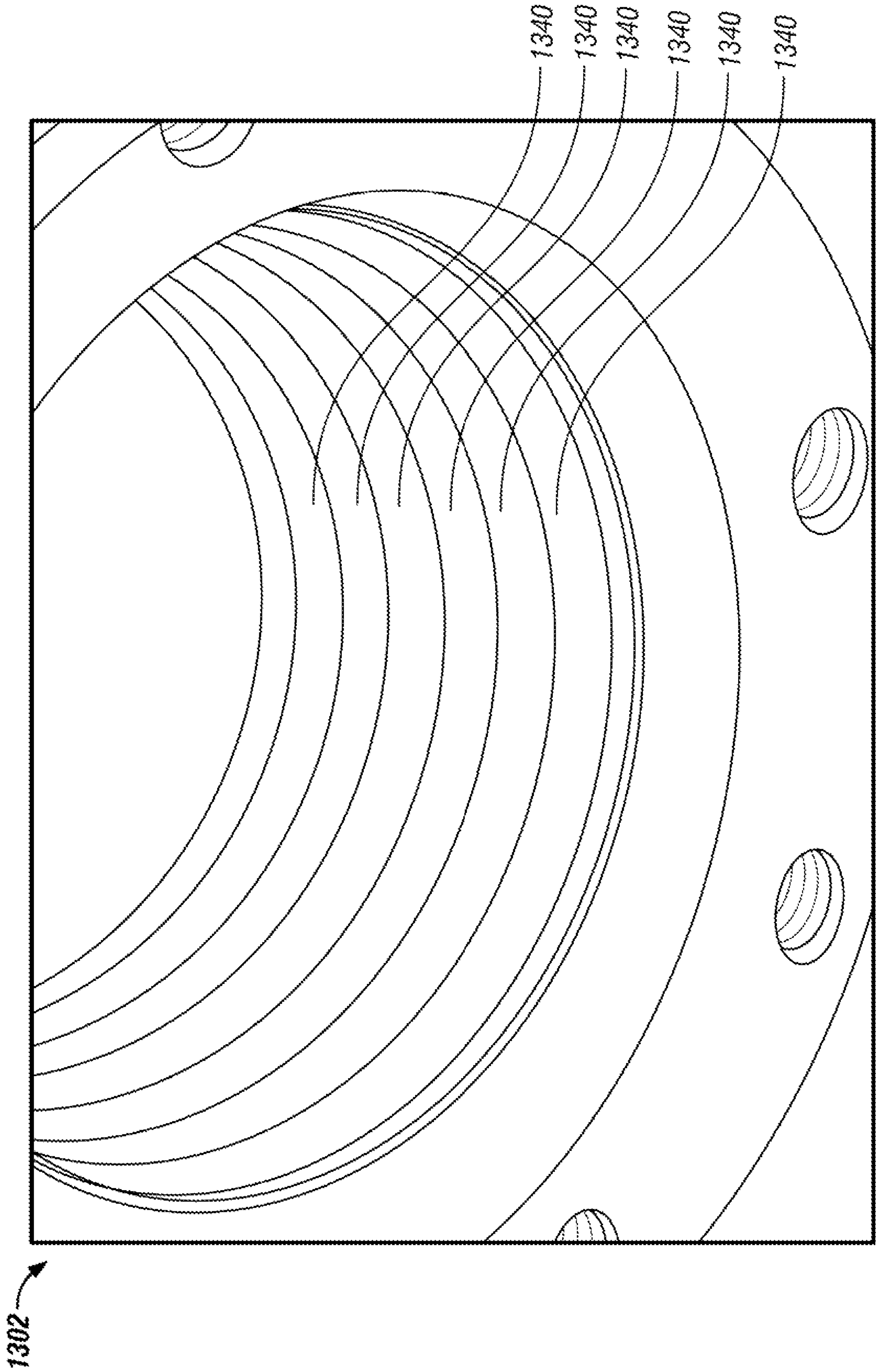
FIG. 13 is a cross sectional illustration of the flex-PCB inside the rDMA housing in accordance with the invention shown in FIG. 3.

Referring also to FIG. 13, there is shown a cross sectional illustration of flex-PCB inside rDMA housing 1302. The flex-PCB (See also FIG. 14-1402) is comprised of three sets of eight pads that form ring electrodes 1340 when installed in the rDMA housing 1302. Each of the Gold Plated Copper Flex-PCB Fabricated Ring Electrodes 1340 serves as a collector on which charged aerosol particles impact. Charge transferred from these charged particles induces a current which is directed to the detection circuitry shown in FIG. 15.

Figure 14:
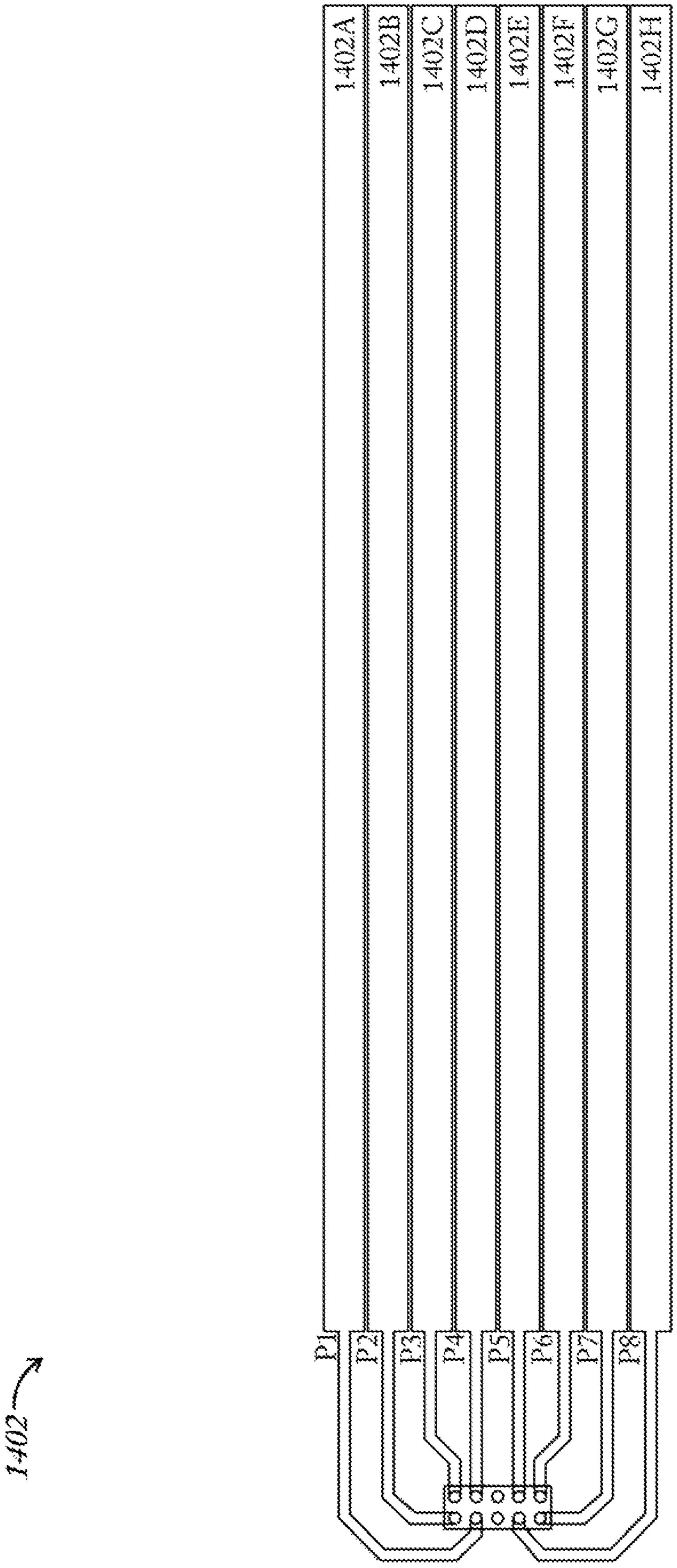
FIG. 14 is an illustrated layout of the flexible Printed Circuit Board (flex-PCB) in accordance with the invention shown in FIG. 13.

Referring also to FIG. 14, there is shown an illustrated layout of the flexible Gold plated Copper on Flexible Substrate Printed Circuit Board 1402. The flex-PCB 1402 comprises a series of electrodes for charge detection. The flex-PCB 1402 wraps around the inside of the reverse Differential Mobility Analyzer housing (rDMA) (See FIG. 2-208) while the smaller traces create a current path to the detection circuitry (See FIG. 15). It will be appreciated that the width and location of each electrode 1402A-1402H can be designed to select specific bands of particle sizes of interest. It will be further appreciated that flexible PCB electrodes 1402A-1402H with integrated electrometers allow for quick removal and cleaning, as well as inexpensive replacement. In addition, PCB electrodes 1402A-1402H minimize electrical noise in the measurements due to lowered capacitive effects of fixed electrodes 1402A-1402H. PCB electrodes 1402A-1402H incorporate inherent bi-polar junction transistors directly on the detection electrodes 1402A-1402H, allowing amplification at the charged particle impaction site 1402A-1402H. The use of printed or thin-film transistors as detection electrodes, as described herein, minimize electrical losses due to resistive materials and also eliminate electrical noise due to the dipole nature of transmission traces. The inherent nature of the PCB electrodes 1402A-1402H transistor provide current amplification at the source of charge transfer, therefore improving overall signal quality.

Figure 15:
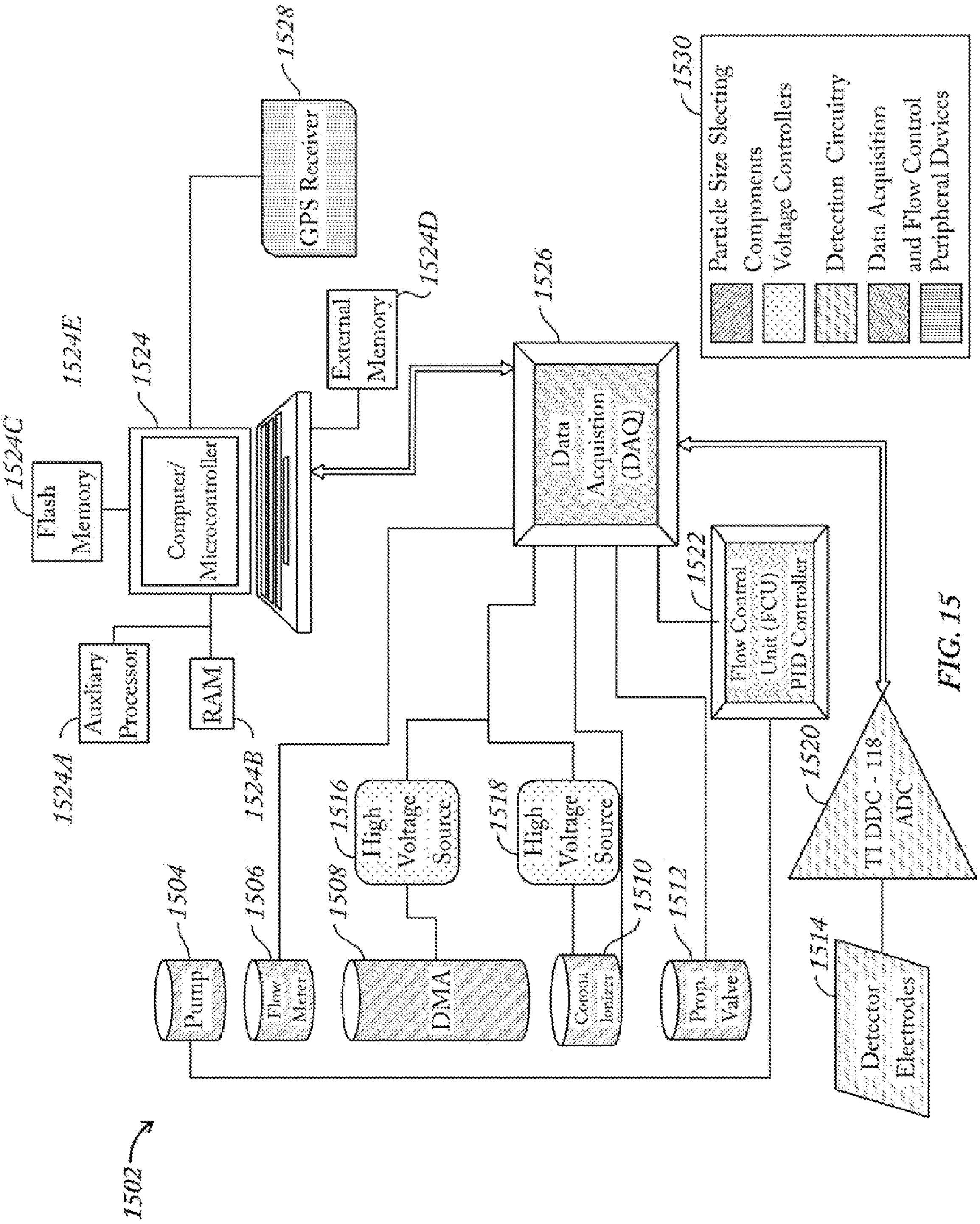
FIG. 15 is a functional flow diagram of the PUPS detection circuitry in accordance with the invention shown in FIG. 1.

Referring also to FIG. 15, there is shown a functional flow diagram 1502 of the PUPS detection circuitry.

Particle Size Selecting Components—This portion of the system is dedicated to discriminating particle size based on electrical mobility. Sample particles are charged in the corona ionizer 1510 and are then incident to electric field induced by high potential which affects the flight path of the particle in the rDMA 1508. The through-device particle velocity is determined by the pump 1504 and proportional valve 1512 creating a closed-loop control system with the flow meter 1506.

Voltage Controllers—The first voltage controller 1518 provides the requisite potential for breakdown in the corona ionizer 1510. The second voltage controller 1516 provides the high potential needed to alter the course of the charged particles to impact on the electrode walls.

Detection Circuitry—The detection circuitry contains the flexible printed circuit board (flex-PCB) electrodes 1514 which the charged particles impact and transfer their charge to as well as the low-current measurement circuitry 1514, 1520 (see legend 1530). It will be appreciated that any suitable low-current measurement circuitry may be used. The signal produced (which has been converted to a digital signal by converter 1520) contains information which can be processed to determine the time-resolved particle concentrations impacting the electrodes.

Data Acquisition and Flow Control—The Data Acquisition section 1526 houses both digital and analog circuitry to monitor system components as well as control the high voltage sources. The Flow Control section 1522 controls the pump and flow rates of the instrument.

Peripheral Devices—The peripheral devices associated with the instrument are optional to the primary objective of the device. In the figure, a Global Positioning System Receiver 1528 is shown allowing particle measurements to occur both in a temporal and spatial system.

Still referring to FIG. 15, computer/microcontroller 1524 may be any suitable computer/microcontroller. For example, computer/microcontroller 1524 may be a “mote”. As used in this disclosure, the term “mote device” or “mote” typically indicates an autonomous or semi-autonomous computing, communication, actuating, and/or sensing device as described in the mote literature (e.g., Intel Corporation’s, or Crossbow Inc.’s mote literature).

Certain embodiments of the mote device(s) 1524 can be fabricated to be relatively small (typically less than several inches in dimension, often a fraction of an inch). Certain embodiments of mote systems(s) (e.g., controller 1524 and data acquisition 1526, GPS receiver 1528) can also be relatively inexpensive to produce, and can be designed to stand up to relatively harsh and/or external environments.

Many embodiments of mote systems(s) 1524, or simply “motes”, as described in this disclosure can provide a wide variety of parameter sensing and/or actuating functionalities. Such parameter sensing may be controlled (and/or light or display device actuated) using computer-based sensing, electro-mechanical sensing, magnetic sensing, and/or other sensing techniques. Certain embodiments of mote device(s) and networks can be located at remote, hostile, external, or inaccessible location(s); and can be wirelessly networked.

Mote 1524 can be programmed with control algorithms for auxiliary circuitry managing activation of sources and sensors, to ensure that energy is expended in an efficient manner, and to dynamically adapt deployments to environmental conditions.

Still referring to FIG. 15 there is shown a programmable mote device 1524, equipped with auxiliary processor 1524A, RAM 1524B and Flash memory 1524C. Optionally, mote 1524 can be augmented with external memory 1524D. Motes also have a communication device 1524E capable of approximately 100 meter communication range, and can support a variety of data retrieval techniques.

It will be appreciated that the invention advantageously incorporates motes 1524 to eliminate the wiring burdens and heavy enclosures often required of traditional data logging mechanisms, and significantly reduces power requirements. The mote system (FIG. 15, item 1524) establishes a standard protocol connection, for example, but not limited to, a TCP/IP connection with another mote system. This standard protocol allows an easy interface to data storage and visualization applications. Furthermore, this TCP/IP connection serves as an actuation channel, for controlling the deployment remotely, for example to modify sampling rates for power management.

It will be appreciated that the invention overcomes prior art limitations with novel features such as: Particle Ionization Particles ionized in the PUPS receive a negative charge via a low cost unipolar corona ionizer. Defining features of the PUPS corona ionizer

- A pin-to-cylinder configuration is used giving the device rotational symmetry.
- A negative kilovolt DC potential sets up a static electric field from pin to cylinder.
- Low cost tungsten microprobes (normally used for semiconductor test applications) form the corona pin. The microprobes have very small tip geometry and tungsten is resistant to corrosion.
- A composite manifold made from virgin electrical grade TEFLON polytetrafluoroethylene (PTFE) and 6061 aluminum alloy serves the dual purpose of making electrical contact and channeling the aerosol around the corona avalanche head to reduce particle fragmentation.
- The body of the corona ionizer is constructed from PTFE due to its electrical and chemical resistance.

Similarly, the advantageous features of the invention's Flexible PCB Detectors also overcome limitations in the prior an. The Flexible Printed Circuit Board (flexPCB) detectors are used for particle detection and allow a circuit to bend to fit geometries which normal printed circuit boards cannot. There are at least four major benefits to using flexPCBs as described in this invention description:

- The flexPCB can easily be removed for cleaning, whereas fixed-ring designs require difficult cleaning procedures which do not ensure complete cleanliness.
- Disposable electrodes can be built due to the relative low cost of the flexPCB.
- The flexPCB can be removed from the DMA allowing chemical samples to be taken based on specific size-bands of particles contacting the electrodes.
- The flexPCB makes it possible to place the electrometer circuit on the electrode itself, thus minimizing signal losses.

It should be understood that the foregoing description is only illustrative of the invention. For example, the PUPS may use a positive corona ionizer for applying a positive charge via a positive high voltage potential to the aerosol particles with suitable modifications to the PUPS rDMA and detection circuitry. Thus, various alternatives and modifications can be devised by those skilled in the art without departing from the invention. For example, the portability of the invention stemming from the light weight and small size of the present invention (approximately 432 cu. in. and approximately 8 lbs, respectively) may be modified slightly. Accordingly, the present invention is intended to embrace all such alternatives, modifications and variances that fall within the scope of the appended claims.

What is claimed is:

1. A portable apparatus for measuring aerosol particle concentration and particle size distribution, the apparatus comprising:

a corona ionizer for applying, a negative charge via a negative kilovolt DC potential to the aerosol particles, wherein the corona ionizer comprises:

at least one tungsten needle;

a concentric ground ring electrode;

a reverse differential mobility analyzer (rDMA) for separating and quantifying aerosol particles based on electrical mobility, wherein the rDMA comprises:

at least one central repulsion electrode;

at least one ground ring electrode; and at least one detection circuit controller.

2. The apparatus as in claim further comprising:

at least one sheath gas injection module providing concentric alignment of the corona ionizer, and at least one sheath gas straightener, wherein the sheath gas injection module comprises:

at least one sheath gas injection port for injecting sheath gas;

at least one sample gas injection port for injecting an aerosol gas sample to be analyzed;

the at least one sheath gas flow straightener promotes laminar flow of the sheath gas; and at least one aerosol injection manifold for centering the at least one central repulsion electrode and promoting tracking of the aerosol gas sample along a surface the at least one central repulsion electrode.

3. The apparatus as in claim 2 wherein the corona ionizer further comprises:

at least one conductive needle support wherein the at least one conductive needle support comprises machined flow pathways for the aerosol gas sample; and at least one non-conductive needle support for supporting the at least one tungsten needle and electrically insulating the at least one conductive needle support from the at least one ground ring electrode, wherein the at least one non-conductive needle support comprises machined flow pathways for the aerosol gas sample.

4. The apparatus as in claim 1 further comprising at least one exhaust gas flow straightener for promoting a constant flow of gas through a radial cross section of the rDMA.

5. The apparatus as in claim 1 wherein the rDMA further comprises:

at least one flexible printed circuit board (PCB) for detecting charged particle induced current; and at least one converter for converting the detected charged particle induced current to a digital signal.

6. The apparatus as in claim 5, wherein the at least one flexible PCB further comprises;

a plurality of first flexible PCBs; and a plurality of second flexible PCBs.

7. The apparatus as in claim 1 further comprising a data acquisition controller for monitoring and controlling the portable apparatus.

8. The apparatus as in claim 1 further comprising a flow controller for controlling sheath gas flow rate and aerosol gas sample rate.

* * * * *